United States Patent
Liu et al.

(10) Patent No.: US 10,820,868 B2
(45) Date of Patent: Nov. 3, 2020

(54) TABLE SYSTEM AND METHOD FOR PET/CT IMAGING

(71) Applicant: SHANGHAI UNITED IMAGING HEALTHCARE CO., LTD., Shanghai (CN)

(72) Inventors: Weiping Liu, Shanghai (CN); Shitao Liu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

(21) Appl. No.: 16/798,521

(22) Filed: Feb. 24, 2020

(65) Prior Publication Data
US 2020/0187886 A1 Jun. 18, 2020

Related U.S. Application Data

(63) Continuation of application No. 15/281,577, filed on Sep. 30, 2016, now Pat. No. 10,568,596.

(30) Foreign Application Priority Data

Jun. 30, 2016 (CN) .......................... 2016 1 0498768
Jun. 30, 2016 (CN) .......................... 2016 1 0498791

(51) Int. Cl.
*A61B 6/00* (2006.01)
*A61B 6/04* (2006.01)
*A61B 6/03* (2006.01)

(52) U.S. Cl.
CPC ............ *A61B 6/4417* (2013.01); *A61B 6/032* (2013.01); *A61B 6/037* (2013.01); *A61B 6/0407* (2013.01); *A61B 6/5235* (2013.01); *A61B 6/488* (2013.01); *A61B 6/5276* (2013.01); *A61B 6/584* (2013.01)

(58) Field of Classification Search
CPC .................................................... A61B 6/5276
See application file for complete search history.

(56) References Cited

U.S. PATENT DOCUMENTS

| | | |
|---|---|---|
| 4,131,802 A | 12/1978 | Braden et al. |
| 7,043,784 B2 | 5/2006 | Plannerer |
| 7,357,575 B2 | 4/2008 | Huber et al. |
| 7,607,833 B2 | 10/2009 | Marzendorfer |

(Continued)

FOREIGN PATENT DOCUMENTS

| | | |
|---|---|---|
| CN | 1759807 A | 4/2006 |
| CN | 100444799 C | 12/2008 |

(Continued)

OTHER PUBLICATIONS

First Office Action in Chinese Application No. 201610498791.4 dated Sep. 4, 2018, 49 pages.

(Continued)

*Primary Examiner* — Dani Fox
(74) *Attorney, Agent, or Firm* — Metis IP LLC

(57) ABSTRACT

The present disclosure provides a table and an imaging system and method for PET/CT imaging. The table may include a base, a bracket, and a plate movable relative to the bracket. The bracket may include a releasing position, a CT scan position, and a PET scan position. The table may extend the scan range of the CT scanner without changing the size of the imaging system.

20 Claims, 9 Drawing Sheets

(56) References Cited

U.S. PATENT DOCUMENTS

| | | |
|---|---|---|
| 7,810,187 B2 | 10/2010 | Van Es et al. |
| 8,511,894 B2 | 8/2013 | Gagnon et al. |
| 2004/0261176 A1 | 12/2004 | Plannerer |
| 2006/0109959 A1 | 5/2006 | Kroner et al. |
| 2006/0174412 A1 | 8/2006 | Hornig |
| 2006/0184012 A1 | 8/2006 | Marzendorfer |
| 2007/0251008 A1 | 11/2007 | Li |
| 2008/0201849 A1 | 8/2008 | Van Es et al. |
| 2010/0034350 A1 | 2/2010 | Vaisburd et al. |
| 2010/0287703 A1 | 11/2010 | Zapata |
| 2011/0152662 A1 | 6/2011 | Khamaisi |
| 2012/0093380 A1 | 4/2012 | Gagnon et al. |
| 2013/0072751 A1 | 3/2013 | Omernick et al. |
| 2013/0298328 A1 | 11/2013 | Singh |
| 2014/0063011 A1 | 3/2014 | Noshi |
| 2014/0177934 A1 * | 6/2014 | Noshi .................. A61B 6/037 382/131 |
| 2015/0135437 A1 | 5/2015 | Li et al. |
| 2015/0196227 A1 | 7/2015 | Chen et al. |
| 2016/0113598 A1 | 4/2016 | Dong |

FOREIGN PATENT DOCUMENTS

| | | |
|---|---|---|
| CN | 102805643 A | 12/2012 |
| CN | 204121039 U | 1/2015 |

OTHER PUBLICATIONS

First Office Action in Chinese Application No. 201610498768.5 dated Aug. 22, 2018, 22 pages.

\* cited by examiner

TABLE SYSTEM AND METHOD FOR PET/CT IMAGING

The application is a continuation of U.S. patent application Ser. No. 15/281,577, filed on Sep. 30, 2016, now U.S. Pat. No. 10,568,596, which claims priority of Chinese Patent Application No. 201610498791.4 filed on Jun. 30, 2016, and Chinese Patent Application No. 201610498768.5 filed on Jun. 30, 2016, the entire contents of each of which are hereby incorporated by reference.

TECHNICAL FIELD

This application generally relates to medical diagnosis, and specifically, relates to a table system and method for PET/CT imaging.

BACKGROUND

With the advance of science and technology, medical imaging has obtained great development, and more imaging modes have become available, such as X-Ray photography, magnetic resonance imaging (MRI), computed tomography (CT), positron emission tomography (PET) and so on, each of which with its strengths may complement each other.

PET is a fairly advanced clinical imaging technique in the field of nuclear medicine. In PET, a positron generated by the decay of a radionuclide gets in collision with a negatron in vivo, then the positron and the negatron are annihilated with each other, two gamma photons are emitted in almost opposite directions. Functional information relating to metabolic activities may be obtained by way of detectable gamma rays to diagnose a disease. A PET image may show the functional information and identify a tumor. However, the resolution of the PET image may be low.

CT is another clinical imaging technique in which a specific part of a body with a certain thickness may be scanned. For instance, when X rays pass through human tissues, a portion of the X rays may be absorbed by the tissues, and a portion passing through the body may be detected by a detector on the basis of which a corresponding signal may be generated. Corresponding to the differences in densities of various tissues and the differences in the x-ray penetration abilities, the detected rays may be different. The signal corresponding to the detected rays may be converted to a digital signal. The digital signal may be processed by a computer, and then an image may be generated and displayed. A minor lesion in vivo may be identified based on the image. The CT may generate an anatomical image with a high resolution and a high sensitivity in identifying the morphology of a tissue. However, CT may lack the capacity to determine other characteristics of the lesion.

PET/CT is a technology combining CT with PET. It may provide the information of CT and PET with only one diagnostic examination using a same table and a same image processing workstation. Fused images may be obtained by image reconstruction and image fusion. The fused images may show both functional and anatomical information. The fused images with more complementary information and higher resolution may improve diagnostic accuracy. For instance, the fused images may provide more information for making a treatment plan for tumor.

A PET/CT fused image may be obtained by superimposing one image on another of a same anatomical location or level. In this case, the vertical position of the table on which a patient may be placed for examination may need to be controlled to facilitate the image fusion.

Usually, a plate of the table supported at only one end may be displaced relative to the CT scanner in an axial direction during a CT scanning. When the plate extends out, because of the weight of a patient placed on the plate, the plate may bend within a scanning cross-section. The scanning cross-section may be a plane perpendicular to the rotation axis and through an iso-center of the CT scanner. The plate may also bend during a PET scanning. The CT image and the PET image at a same anatomical location or level may need to be matched so that the CT image and the PET image may be fused. Hence, the bending of the plate may need to be corrected in order to match a CT image with a corresponding PET image.

Besides, in the PET/CT system as illustrated in FIG. 1(a), a table unit 13 includes a base 133, a bracket 132 and a plate 131. Plate 131 may move relatively to the bracket 132 along the axial direction. There is a position 1331 for a CT scan (shown as a dotted line in FIG. 1(a)) and a position 1332 for a PET scan (shown as a dotted line in FIG. 1(a)) on the base 133 along the z axis parallel to the rotation axis of the CT scanner 11 (i.e., the length direction of the plate 131). When the bracket 132 is placed at position 1331 for a CT scan, a patient may be placed onto or removed from the table unit 13 (e.g., the plate 131 of the table unit 13). The plate 131 may exit from the bore of CT scanner 11 completely to avoid collision with CT scanner 11 when the plate 131 is moved up or down. In this case, the distance between one end of the plate 131 close to CT scanner 11 and the scanning cross-section is large. CT scan may not be performed before the plate 131 arrives at the scanning cross-section. In the case of a fixed maximum moving distance of the plate 131, the further an initial position of the plate 131 is away from the scanning cross-section, the smaller the scanning range of CT scanner 11 is.

SUMMARY

A first aspect of the present disclosure relates to a table. The table may include a base, a bracket, and a plate. The plate may be configured to move relatively to the bracket. There may be various positions on the base along a length direction of the plate including a position at which a patient may be placed onto or removed from the table (or referred to as a releasing position), a position for CT scan (or referred to as a CT scan position), and a position for PET scan (or referred to as a PET scan position). When the bracket is placed at the releasing position, the position of the plate is adjustable (e.g., by moving the plate up or down) and the distance between the floor and the plate may be in the range from 450 mm to 1000 mm, from 500 mm to 1000 mm, from 550 mm to 950 mm, or from 550 mm to 945 mm. When the bracket is placed at the CT scan position, the position of the plate is adjustable (e.g., by moving the plate up or down) and the distance between the floor and the plate may be in the range from 700 mm to 1000 mm, from 750 mm to 1000 mm, from 800 mm to 950 mm, or from 820 mm to 945 mm. The plate is movable (e.g., by moving the plate up or down) for a first distance from the floor when the bracket is placed at the PET scan position of the base and the plate is movable (e.g., by moving the plate up or down) for a second distance from the floor when the bracket is placed at the CT scan position, wherein the first distance is the same as the second distance.

A second aspect of the present disclosure relates to a PET/CT system. The PET/CT system may include a CT scanner configured to perform CT scanning, a PET scanner configured to perform PET scanning, and a table unit. The table unit may include a base, a bracket, and a plate. The plate may be configured to move relatively to the bracket. There is a releasing position, a CT scan position, and a PET scan position on the base of the table unit. When the bracket is placed at the releasing position, the position of the plate is adjustable (e.g., by moving the plate up or down) and the distance between the floor and the plate may be in a range from 450 mm to 1000 mm, from 500 mm to 1000 mm, from 550 mm to 950 mm, or from 550 mm to 945 mm. When the bracket is placed at the CT scan position, the position of the plate is adjustable (e.g., by moving the plate up or down) and the distance between the floor and the plate may be in a range from 700 mm to 1000 mm, from 750 mm to 1000 mm, from 800 mm to 950 mm, or from 820 mm to 945 mm. The plate is movable (e.g., by moving the plate up or down) for a first distance from the floor when the bracket is placed at the PET scan position of the base and the plate is movable (e.g., by moving the plate up or down) for a second distance from the floor when the bracket is placed at the CT scan position, wherein the first distance is the same as the second distance. A maximum scan range of the CT scanner may be from 1700 mm to 2100 mm, 2060 mm, 2000 mm, 1960 mm, or 1900 mm. The PET scanner may achieve a whole body scan with one scan. A field of view of the PET scanner may be from 1700 mm to 2000 mm, from 1800 to 2000 mm, or from 1900 mm to 2000 mm.

In some embodiments, the PET/CT system may further include a measuring unit and a height adjustment unit. The measuring unit may be configured to measure the distance of the plate from the floor (or referred to as the height of the plate) at the scanning cross-section during the CT scanning. The height adjustment unit may be configured to adjust the height of the plate according to the height of the plate measured by the measuring unit during the CT scanning.

In some embodiments, the PET/CT system may further include an obtaining unit configured to obtain images, a determining unit configured to determine a relationship between the heights of the plate from a floor in the images and the distances of the plate moving along the length direction of the plate (or referred to as the axial direction), and a height adjustment unit configured to adjust the height of the plate according to the relationship such that the movement (including, for example, the movement along the length direction, the height adjustment, and the bending) of the adjusted plate fitting the relationship. The images may be CT images or topograms. In some embodiments, the relationship may be linear or essentially linear. In some embodiments, the relationship may be non-linear.

In some embodiments, the PET/CT system may further include a correcting unit configured to correct a position error of the plate during the PET scanning compared to the CT scanning.

In some embodiments, the PET/CT system may further include a correcting unit configured to correct data acquired in the PET scanning.

A third aspect of the present disclosure relates to a method for PET/CT imaging. The method may include loading a patient when the bracket is placed at a releasing position, performing a CT scan when the bracket is placed at the position for CT scan and performing a PET scan when the bracket is placed at the position for PET scan.

In some embodiments, the method may include adjusting a first height of the plate from the floor according to a second height of the plate from the floor at the scanning cross-section during the CT scanning so that a changing trend of the first height of the adjusted plate from the floor is consistent with a changing trend of the second height of the plate from the floor during the CT scanning. In some embodiments, the adjustment may be made before performing a PET scan.

In some embodiments, the method may include obtaining CT images or topograms, determining the relationship between the heights of the plate from the floor in the CT images or topograms and the distances of the plate moving in the length direction of the plate, and adjusting the plate according to the relationship to make the movement of the adjusted plate fitting the relationship. In some embodiments, the relationship may be linear or essentially linear.

In some embodiments, the method may include correcting the PET data after performing a PET scan.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1A:
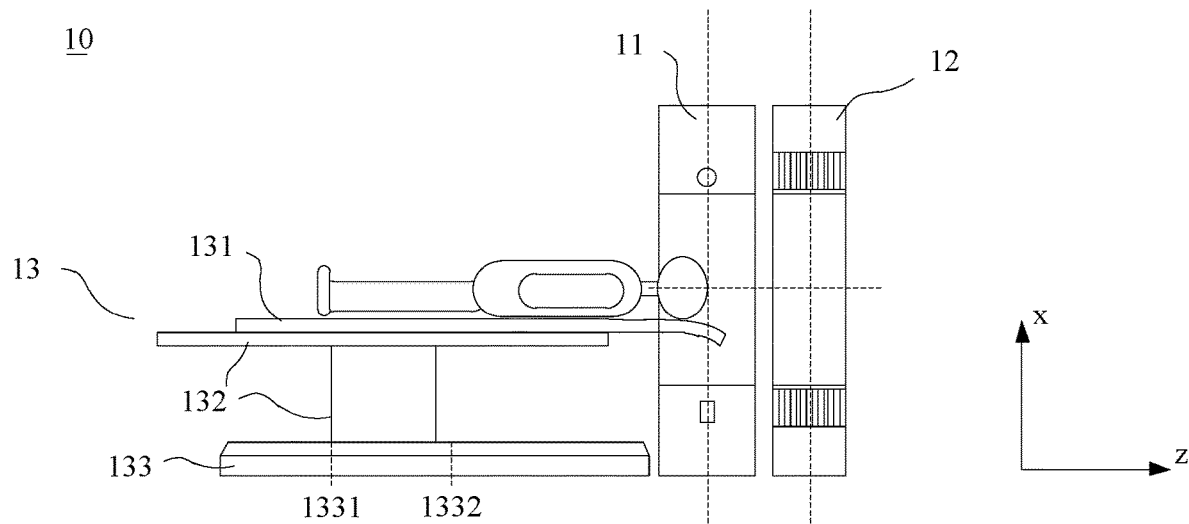
FIG. 1(a) is a diagram of a prior art PET/CT system in which a CT scan is being performed.

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

It will be understood that the term "system," "unit," "module," and/or "block" used herein are one method to distinguish different components, elements, parts, section or assembly of different level in ascending order. However, the terms may be displaced by other expression if they may achieve the same purpose.

It will be understood that when a unit, engine, module or block is referred to as being "on," "connected to" or "coupled to" another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include," and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

In an imaging system or a method according to the present disclosure, a relationship between the heights of the plate from a floor and the distances of the plate moving in an axial direction (or a length direction) of the plate is determined from images in advance. The plate may be adjusted so that the movement of the plate (including, for example, the movement along the axial direction, the height adjustment, and the bending of the plate) may conform to the relationship. At this point, an image of a patient may be obtained. Scan data may be corrected according to the position error between a height of the plate from the floor in previously acquired images and a height of the plate from the floor during imaging. The previously acquired images and the current images may be matched to facilitate image fusion. The imaging system or method according to the present disclosure may compensate a difference of the bending of the plate between different imaging modes. Consequently, the image matching or fusion may be simplified and the quality of image fusion may be improved. The system in the present disclosure may be CT, MRI, PET or any combination thereof. In the following embodiments of the present disclosure, a PET/CT system combining CT with PET described below is merely provided for illustration purposes, and not intended to limit the scope of the present disclosure.

Figure 1B:
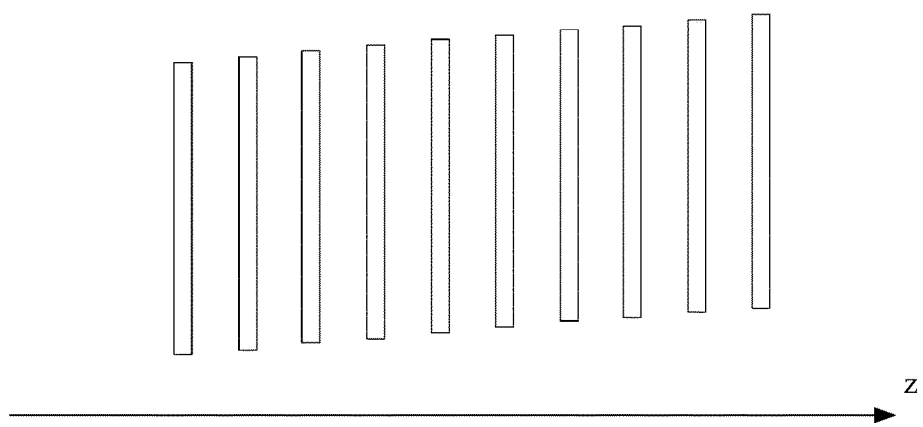
FIG. 1(b) is a diagram illustrating the bending of the plate of a table in a CT scan.
Figure 2A:
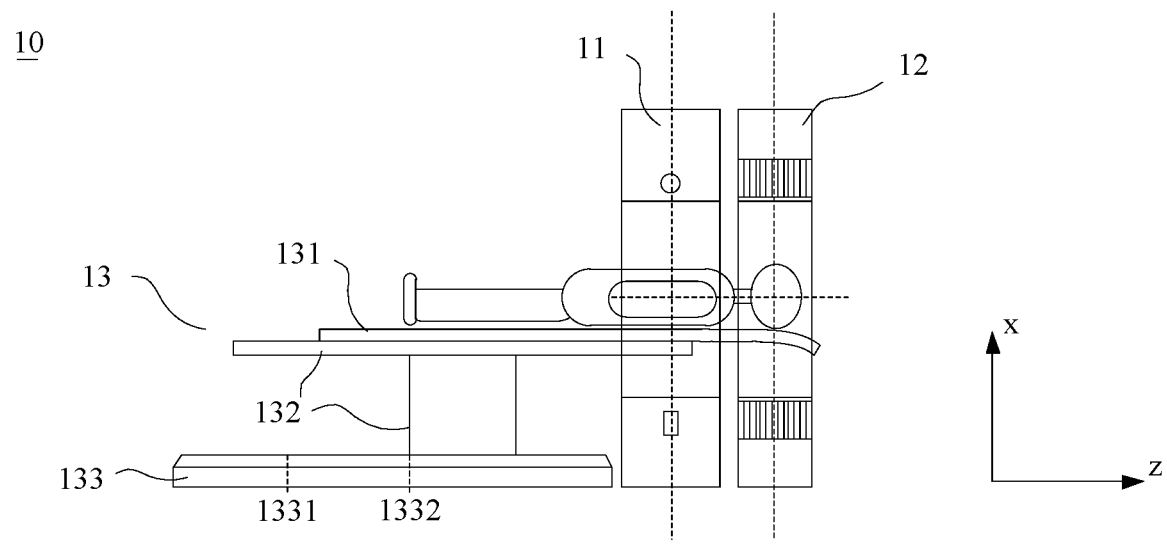
FIG. 2(a) is a diagram of a prior art PET/CT system in which a PET scan is being performed.
Figure 2B:
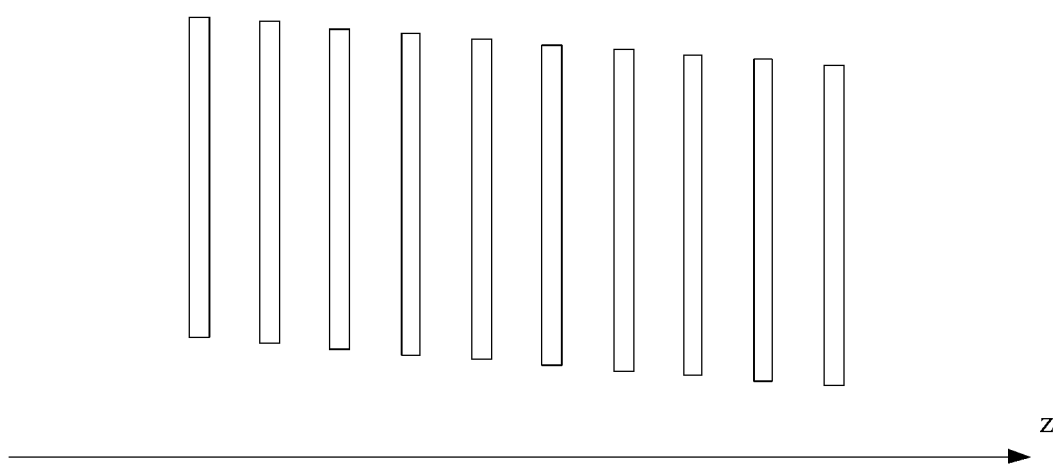
FIG. 2(b) is a diagram illustrating the bending of the plate of a table in a PET scan.

FIG. 1(a) is a diagram of a prior art PET/CT system in which a CT scan is being performed; FIG. 1(b) is a diagram illustrating the bending of the plate of a table in a CT scan; FIG. 2(a) is a diagram of a prior art PET/CT system in which a PET scan is being performed; FIG. 2(b) is a diagram illustrating the bending of the plate of a table in a PET scan.

With reference to FIG. 1(a), a PET/CT system may include a CT scanner 11, a PET scanner 12, and a table unit 13. The CT scanner 11 may be configured to run a CT scan and the PET scanner 12 may be configured to run a PET scan. The table unit 13 may include a base 133, a bracket 132 and a plate 131. The plate 131 may be configured to move relatively to the bracket 132 in an axial direction. There may be a position 1331 for CT scan (shown as dotted line) and a position 1332 for PET scan (shown as dotted line) on the base 133 along z axis which is parallel to a rotation axis of the CT scanner 11 (i.e., length direction of the plate 131). The bracket 132 at position 1331 may be used for CT scan, and the bracket 132 at position 1332 may be used for PET scan. The table 131 may be configured to support and transport the patient from a region to be imaged to a scanning cross-section of CT scanner 11 or a field of view (FOV) of PET scanner 12. Wherein the scanning cross-section is a plane perpendicular to the rotation axis and through an iso-center of the CT scanner 11. Usually, the distance between position 1331 and position 1332 along z axis may be equal to the distance between the iso-center of the CT scanner 11 and the center of FOV of the PET scanner 12.

As shown in FIG. 1(a), during the CT scanning, the bracket 132 may be placed at position 1331, and the plate 131 supporting the patient moves along the positive direction of the z axis t, and transfer the region to be imaged (e.g., head of the patient) to the scanning cross-section of the CT scanner 11. An x-ray tube of the CT scanner 11 may be configured to emit radiation rays and a detector of the CT scanner 11 may be configured to detect radiation rays traverses the region to be imaged. And then a reconstruction unit may be configured to reconstruct CT images based on a processed detected signal.

During the CT scanning, the plate 131 may bend when moving towards the CT scanner 11 because of the weight of the patient and/or the weight of the plate itself. The further the plate 131 extends out, the more the plate 131 may bend. For different positions of the plate 131 at the scanning cross-section, the height of the plate 131 at the scanning cross-section may be different. The height of the plate 131 may be the distance between the plate 131 and the floor on which the table (e.g., the base of the table) is placed. In the CT images so acquired, the bending of the plate 131 may increase along an inverse direction of the z axis, as shown in FIG. 1(b). Please note that the bending of the plate 131 shown in FIG. 1(b) is exaggerated for illustration purposes.

As shown in FIG. 2(a), during a PET scanning, the bracket 132 at position 1332 and the plate 131 may operate in concert to transfer the region to be imaged of the patient to the FOV of the PET scanner 12. The plate 131 may bend due to the weight of the patient and/or the weight of the plate 131 itself. During a PET scanning, the plate 131 may be stationary. In the PET images so acquired, the bending of the plate 131 may increase along a positive direction of the z axis, as shown in FIG. 2(b). Please note that the bending of the plate 131 shown in FIG. 2(b) is exaggerated for illustration purposes.

Comparing CT images in FIG. 1(b) with PET images in FIG. 2(b), the trends of the bending of the plate 131 in these two imaging modes are different. Because the distance between position 1331 and position 1332 is equal to the distance between the iso-center of the CT scanner 11 and the center of FOV of the PET scanner 12, the bending of the plate 131 at or around the portion corresponding to the middle of the region to be imaged in a CT image may be approximately equal to the bending of plate 131 in a corresponding PET image. The bending of other portions of the plate 131 in the CT image may be different from the bending of the plate in the corresponding PET image.

As described in background, for PET/CT, an image showing both functional and anatomical information may be obtained by fusing a CT image and a PET image.

Figure 3:
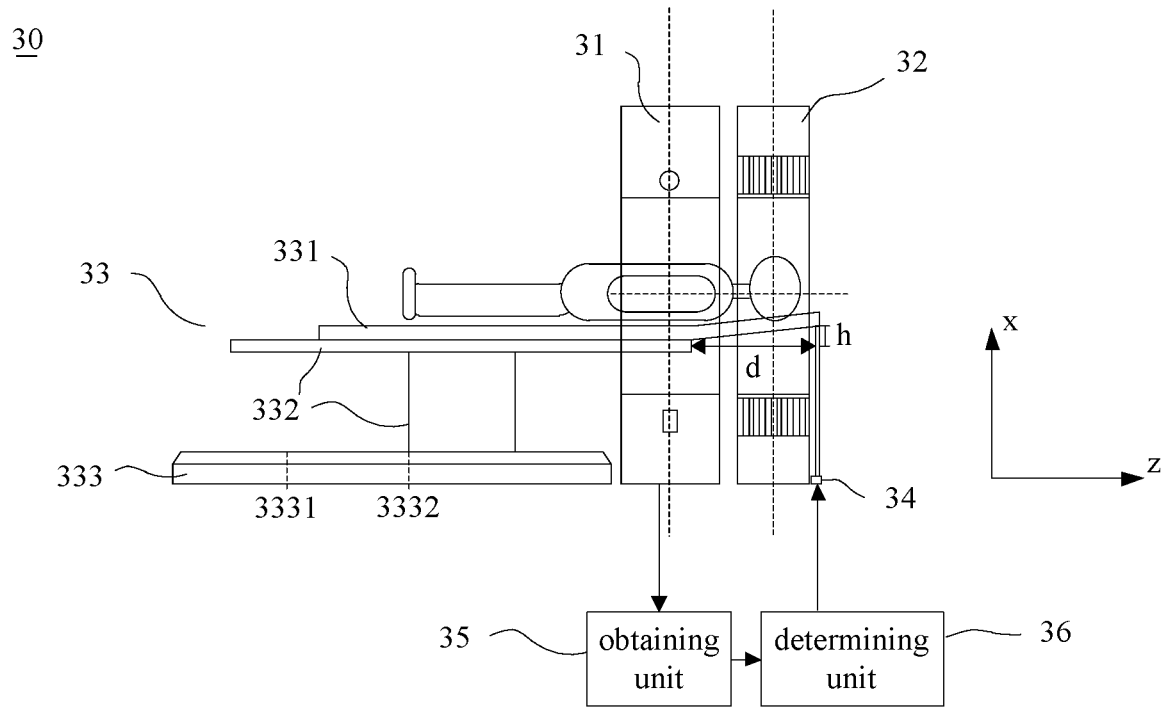
FIG. 3 illustrates an exemplary PET/CT system according to some embodiments of the present disclosure.

To improve the accuracy of fused images, an imaging system in some embodiments of the present disclosure may compensate a difference in the bending of the plate 131 between different imaging modes. With reference to FIG. 3, a diagram illustrating an exemplary PET/CT system according to some embodiments of the present disclosure. The PET/CT system 30 may include a CT scanner 31, a PET scanner 32, and a table unit 33. In some embodiments, the CT scanner 31 and the PET scanner 32 may be coaxial. In some embodiments, the CT scanner 31 and the PET scanner 32 may be non-coaxial. The table unit 33 may include a base 333, a bracket 332, and a plate 331. The plate 331 may be configured to move relatively to the bracket 332 along a length direction of the plate 331. There is a position 3331 for CT scan (indicated by a dotted line) and a position 3332 for PET scan (indicated by a dotted line) on the base 333 along the z axis. The z direction may be parallel to the rotation axis of the CT scanner 31 (also the length direction of the plate 331). When the bracket 332 placed at position 3331, a CT scan may be performed. When the bracket 332 placed at position 3332, a PET scan may be performed. The plate 331 may be configured to support and/or transport the patient so that the region to be imaged may be moved to the scanning cross-section of the CT scanner 31 or a field of view (FOV) of the PET scanner 32. As used herein, the scanning cross-section is a plane through the iso-center and perpendicular to the rotation axis of the CT scanner 31. There is a height adjustment unit 34 on one side of the PET scanner 32 away from the CT scanner 31. By adjusting the plate 331 according to the height of the plate 331 at the scanning cross-section during the CT scanning, a changing trend of the height of the plate 331 during the CT scanning may be reproduced or mimicked.

To control the height adjustment unit 34 to drive the plate 331 and to compensate a difference in the bending of the plate 331 between the CT imaging mode and the PET imaging mode, the PET/CT system 30 may further include an obtaining unit 35 and a determining unit 36.

The obtaining unit 35 may be configured to obtain images. In FIG. 3, the obtaining unit 35 may be connected to the CT scanner 31. In some embodiments, the obtaining unit 35 may acquire a CT image, instead of CT scan data. The CT scan data may be sent to a data acquisition unit and then reconstructed in an image reconstruction unit to generate the CT image provided to the obtaining unit 35. In some embodiments, obtaining CT images is merely provided for illustration purposes, and not intended to limit the scope of the present disclosure. As used herein, CT images may be computed tomographic images.

In some embodiments, the images obtained by the obtaining unit 35 may be topograms. As used herein, a topogram may be a photograph acquired by setting the radiation source at a certain projection angle. In some embodiments, CT images and topograms may be obtained through the CT unit 31 of the PET/CT system 30, or through one or more stand-alone CT apparatuses. In some embodiments, the CT images or topograms may be images retrieved from a storage.

The determining unit 36 may be configured to determine a relationship between the heights of the plate in the images (e.g., CT images, topograms, etc.) and the distances of the plate moving in the axial direction of the plate.

In some embodiments, a coordinate system may have its origin set at the iso-center of the CT scanner 31. Every pixel in a CT image may have a coordinate value. A minimal coordinate value in the x axis of the pixels corresponding to the plate 331 of CT images may be designated as a lowest point of the plate 331. The coordinate value in the x axis of the lowest point may represent a height of the plate 331. The height of the plate 331 may be the distance of the plate 331 from the floor on which the table unit 33 is placed. Thus, the height of the plate 331 in a CT image may be obtained by analyzing CT images. Coordinate values of the other pixels may be selected to represent the height of the plate 331. The height of the plate 331 of CT images may be obtained by other means. For example, a measuring unit may measure the height of the plate 331 when the different portions of the plate 331 pass through the scanning cross-section. As another example, a distance measuring unit may measure the distance along the x axis between the portion of the plate 331 at the scanning cross-section and the distance measuring unit. The distance measuring unit may be a sonar or a laser rangefinder. Other devices that may measure the height of the plate 331 are within the scope of present disclosure.

During the CT scanning, a displacement of the plate 331 along the z axis may be recorded. According to the height of the plate 331 in CT images and the displacement of the plate 331, a relationship between the heights and the displacements of the plate 331 may be determined. In some embodiments, the relationship between the heights and the displacements of the plate 331 may be approximately linear. In some embodiments, the relationship between the heights and the displacements of the plate 331 may be determined by linear fitting. The displacements of the plate 331 may be the same as or relate to the distances of the plate moving in the axial direction. The shorter the scanning range is, the closer to being linear the relationship between the bending or the heights and the displacement of the plate 331 may be. In some embodiments, the gradient of the linear relationship may be the ratio of a change in the bending to the corresponding change in the displacement of the plate 331 based on a geometric relationship. For example, the ratio of the maximum change in the bending to the maximum relative displacement of the plate 331 may be calculated to obtain the gradient of the linear relationship. As used herein, the maximum change in the bending of the plate 331 may refer to the maximum difference between the height of a first portion of the plate 331 in a first CT image and the height of a second portion of the plate 331 in a last CT image. As used herein, the maximum relative displacement may refer to the difference between the position of the plate 331 in the z axis corresponding to the first CT image and the position of the plate 331 in the z axis corresponding to the last CT image. The gradient of the linear relationship may be symbolized by a parameter k. In some embodiments, the linear relationship may be symbolized by one or more other parameters, for example, an angle with respect to the z axis.

The plate 331 may be adjusted by the height adjustment unit 34 to conform to the linear relationship.

As shown in FIG. 3, the plate 331 may be supported by the bracket 332. When the height adjustment unit 34 drives one end away from the bracket 332 of the plate 331 to move in a positive direction of the x axis, the plate 331 may not be separated from the bracket 332 completely. One unsupported end of the plate 131 may be raised by the height adjustment unit 34 to tilt the plate 331, such that a surface of the plate 331 may rise in a positive direction of the z axis.

For example, the height adjustment unit 34 may be installed underneath the plate 331. The height adjustment unit 34 may include a drive element configured to provide a driving force, a transform element configured to transform a rotation movement to a linear movement, and a transfer element connected to the transform element. The drive element may be, for example, a motor, etc. The transform element may include a lead screw and a nut. When the motor operates, the lead screw driven by the motor may rotate, and the nut may move in a straight line along the x axis. Meanwhile, the transfer element may move in a straight line together with the nut. The transfer element may drive one end of the plate 331 to rise together, as shown in FIG. 3.

The height adjustment unit 34 may adjust the height of the plate 331 to be level first, and then continue to raise one end of the plate 331. The distance between the bracket 332 and the height adjustment unit 34 in the z axis is symbolized by a parameter d. The distance of one end of the plate 331 away from the bracket 332 raised from the level is symbolized by a parameter h. The distance h may be monitored while the plate rises. A determination may be made as to whether the relationship among k, h, and d satisfies the following formula (1). If the formula (1) is satisfied, the plate 331 may have been adjusted in place. Otherwise, the plate 331 the plate 331 may continue to be adjusted as to the height of the plate 331.

$$k = \frac{h}{d}. \tag{1}$$

There are many ways of monitoring the distance h in real time. For example, an encoder may monitor the rotation of the motor in order to monitor the distance h in real time. As another example, a distance measuring unit installed on the floor may monitor the distance h in real time by monitoring the distance between one end of the plate 331 and the distance measuring unit. Other devices for measuring the distance h are within the scope of the present disclosure and won't be enumerated here.

The height adjustment unit 34 may include a device configured to drive one end of the plate 331 to rise and are not enumerated here. The height adjustment unit 34 may be installed on the floor, or on the gantry of the PET scanner 32. The height adjustment unit 34 may drive the plate 331 to move in the x axis and not affect imaging. The method and the location of installment of the height adjustment unit 34 are not limited to those exemplified in the present disclosure.

If the relationship among k, d, and h satisfies the formula (1), the shape of the plate 331 may be kept and a PET scan may be performed. PET images may be obtained by reconstructing the PET scan data. The changing trend of the height of the plate 331 in the PET images may conform to the linear relationship. The relationship may be linear or essentially linear. The relationship may represent the changing trend of the height of the plate 331 in the CT images or topograms. Accordingly, the PET/CT system in the some embodiments may obtain CT images and PET images with the same or essentially the same changing trends of the height of the plate 331. The problem of different changing trends of the height of the plate 331 in different imaging modes may be solved. The fusion or matching of the images obtained in different imaging modes may be simplified.

Figure 4:
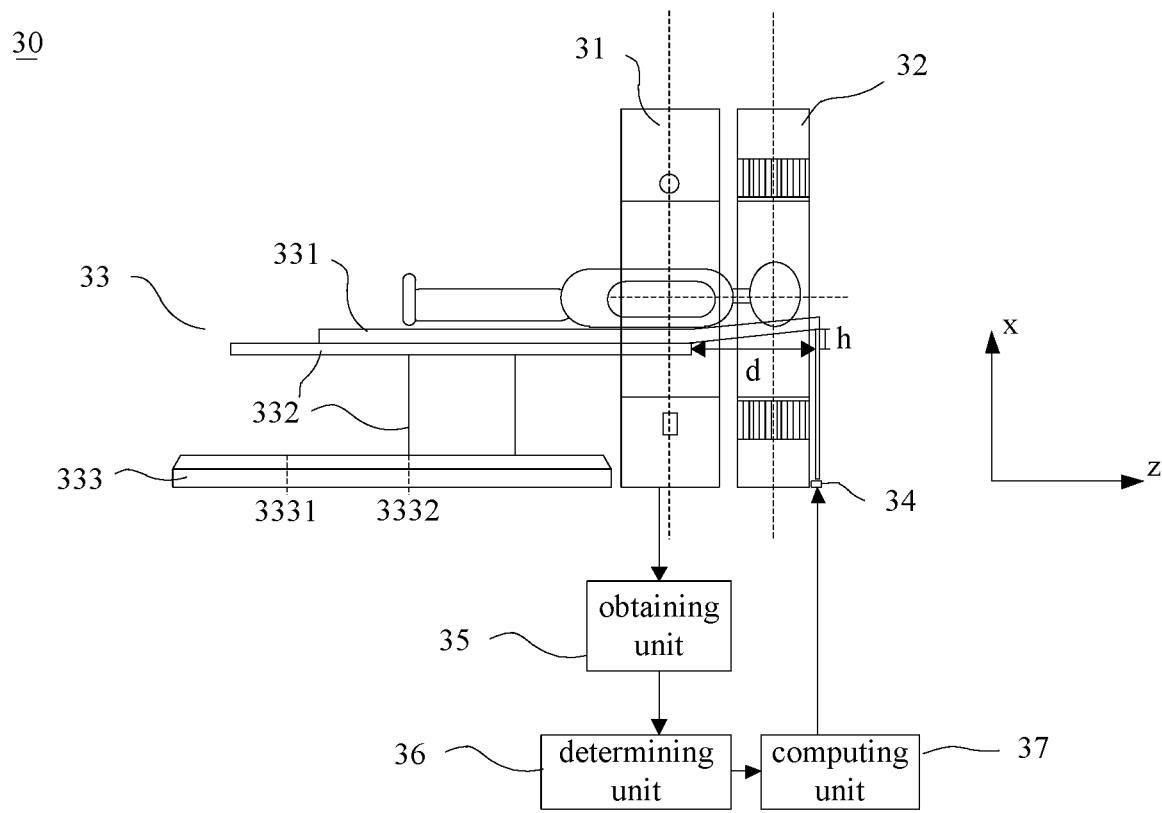
FIG. 4 is a diagram illustrating an exemplary PET/CT system according to some embodiments of the present disclosure.

FIG. 4 illustrates an exemplary PET/CT system according to some embodiments of the present disclosure. The PET/CT system is similar to the PET/CT system illustrated in FIG. 3. The PET/CT system in FIG. 4 may include a computing unit 37 configured to compute a distance of the plate 331 that needs to be raised according to the relationship determined by the determining unit 36 described above.

For example, the gradient k may be obtained by the determining unit 36. The distance d between the bracket 332 and the height adjustment unit 34 in the z axis may be obtained as described elsewhere in the present disclosure. The distance $h_0$ of one end of the plate 331 away from the bracket 332 that needs to be raised from the horizontal level may be computed by the computing unit 37 according to the above formula (1). Then the height adjustment unit 34 may raise the end of the plate 331 by $h_0$ from the horizontal level. Similar with the description with reference to FIG. 3, the height adjustment unit 34 may drive the plate 331 to a horizontal level, and then continue to drive the end of the plate 331 away from the bracket 332 to be raised by $h_0$ in the positive direction of the x axis so that the surface of the plate may fit the relationship described above. A PET scan may be performed. The problem of the different changing trends of the height of the plate in the CT imaging mode and the PET imaging mode may be solved. More descriptions may be found elsewhere in the present disclosure. See, for example, FIG. 3 and the description thereof.

In the embodiments illustrated in FIG. 3 or FIG. 4, the position of the plate 331 in a CT image may be below the horizontal level, while the position of the plate 331 in a PET image may be above the horizontal level. The position error, symbolized by a parameter Δ, may exist between the CT image and the PET image for a same slice. A changing trend of a position of the plate in the CT image mode and a changing trend of the same position of the plate in the PET imaging mode may be essentially the same. Thus the position error Δ between each slice of a CT image and a corresponding portion of a PET image in the x axis may be approximately equal. As used herein, a portion of a PET image may be referred to as corresponding to a slice of a CT image when the portion of the PET image and the slice of the CT image represent or depict a same portion of an object that is scanned. The position error Δ may be corrected to compensate the difference of the height of the plate between the CT imaging mode and the PET imaging mode and to match a CT image with a corresponding PET image.

Figure 5:
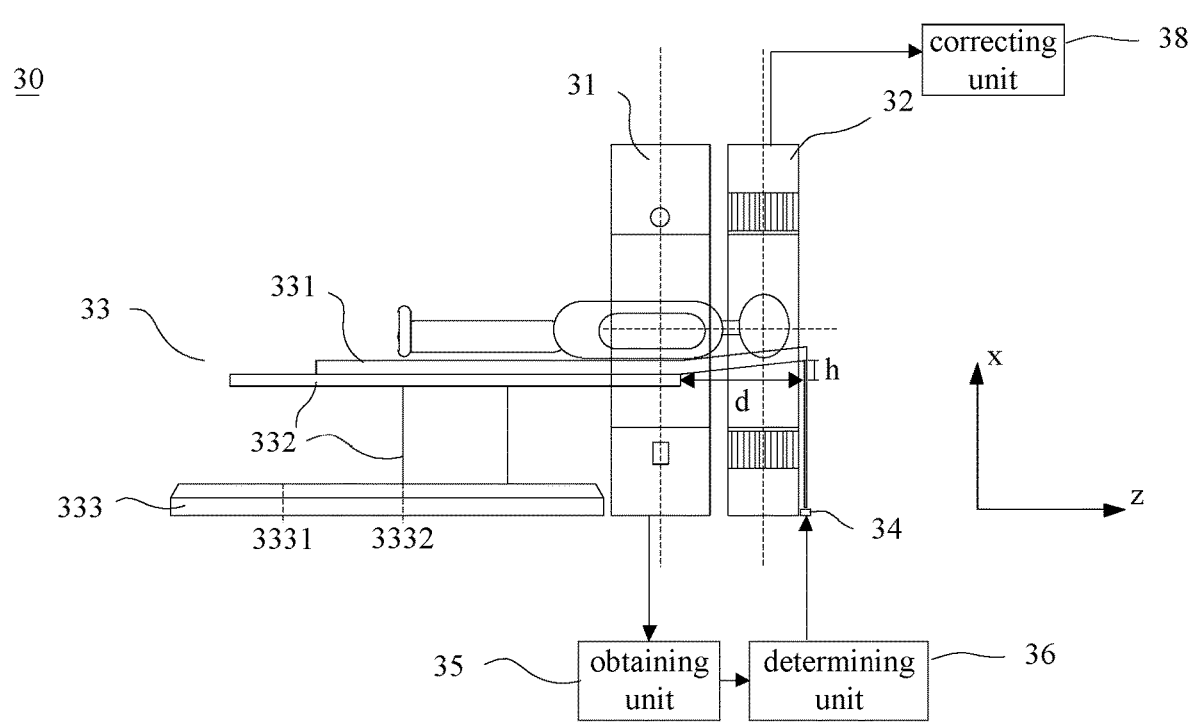
FIG. 5 is a diagram illustrating an exemplary PET/CT system according to some embodiments of the present disclosure.

FIG. 5 is a diagram illustrating an exemplary PET/CT system according to some embodiments of the present disclosure. With reference to FIG. 5, the PET/CT system may include a correcting unit 38 configured to correct the position error of the plate between the CT imaging mode and the PET imaging mode. Position errors in different systems may be different and may be obtained by experiments.

Experiments may be conducted using a water phantom and loads of different weights in the PET/CT system. CT images may be obtained by performing CT scans. The relationship between the heights of the plate and the distances of the plate moving in the axial direction may be determined based on CT images. Then the plate may be adjusted so that the heights of the plate conform to the relationship. PET images may be obtained by performing a PET scan at a height.

Each position error of the plate between the CT image and the PET image in the x axis for each slice may be determined, and the mean value of all position errors may be used as the final position error Δ.

To assess the position error Δ more accurately, the experiment may be repeated for multiple times using a water phantom and loads of different weights (e.g., wedges of different weights, etc.). For each load, multiple position errors $\Delta_1, \Delta_2, \ldots, \Delta_n$ may be obtained, in which n≥1 and n represents the times of the experiments. The times of the experiments for at least two loads of different weights may be the same or different. For each load, the mean value of $\Delta_1, \Delta_2 \ldots \Delta_n$ may be determined and used as the final position error Δ.

The position errors Δ for loads of different weights may be obtained by experiments and may be stored for future use. The position errors Δ may be acquired directly based on the weight of a patient during a scan when needed. In some embodiments, after a PET scan, the correcting unit 38 may acquire the position error Δ corresponding to the patient and correct the data acquired in the PET scanning. The reconstruction unit of the PET scanner 32 may reconstruct the corrected data to obtain the PET images in which the positions of the plate of PET images may match the positions of the plate in the CT images. Because such experiments may be performed for a limited number of times, the number of position errors that may be obtained by experiments is limited. The weight of a patient may vary widely. When the weight of a patient is not already determined by experiment, the position error may be obtained by interpolation or extrapolation.

As illustrated in FIG. 5, the region to be examined is the head of a patient. In this case, the scanning range is short and the position error may be minor, for example, about a few millimeters. In some embodiments, the correcting unit 38 may correct the position error as follows.

The obtaining unit 35 may be configured to obtain images. The images may be CT images or topograms. The determining unit 36 may be configured to determine the relationship between the heights of the plate in the images and the distances of the plate moving in the axial direction. The height adjustment unit 34 may be configured to adjust the height of the plate based on the relationship, in order to make the movement of the adjusted plate fit the relationship. The correcting unit 38 may be configured to acquire the position error Δ based on the patient and send it to the controller of the table unit 33 and the height adjustment unit 34 such that the entire plate may be lowered by Δ in the x axis. In this case, the PET images in which the positions of the plate match the positions in CT images may be obtained by performing a PET scan. In some embodiments, the distance Δ may be short, and thus the region to be examined may be still substantially within the center of FOV of the PET scanner 32.

In some embodiments, the PET/CT system may operate as follows. The obtaining unit 35 may be configured to obtain images. The images may be CT images or topograms. The determining unit 36 may be configured to determine the relationship between the heights of the plate in the images and the distances of the plate moving in the axial direction. The relationship may be linear or approximately linear. The correcting unit 38 may be configured to acquire the position error Δ corresponding to a patient and send the position error Δ to the controller of the table unit 33. The controller may make the plate 331 lower by Δ in the x axis. The height adjustment unit 34 may be configured to adjust the height of the plate according to the relationship such that the movement of the adjusted plate (including, for example, the movement along the axial direction, the height adjustment, and the bending of the plate) may fit the relationship. In this case, the PET images where the positions of the plate match the positions of the plate in the CT images may be obtained by performing a PET scan.

In the PET/CT system, the changing trends of the positions of the plate in CT images and in the PET images may be adjusted to be substantially the same. Then the position error between a CT image and a PET image may be corrected based on the experimental data in the PET image in which the spatial positions and/or spatial coordinates of the PET image may match those in the CT image, thereby facilitating image fusion. In some embodiments an exemplary PET/CT system has been described. It is understood that the imaging system may be a single-mode system or a multi-mode system, such as a separated PET system, an MRI system, and so on, in which the difference of the bending of the plate compared with another imaging system (for example, a CT system) may be compensated.

Merely by way of example, the region to be examined is the head of the patient. When the scanning range is long, for example, in a whole body scan, at least a portion of the plate may bend greatly, and thus the need to compensate the height of the plate may be great.

Usually, the scan range of the PET unit 32 is about 200 mm in a single scan. The plate 331 may be moved in the z axis for many times to perform multiple PET scans if a whole body scan is to be performed on a patient. In the case, the height of the plate may be adjusted according to the process described elsewhere in the present disclosure, so that the changing trend of the height of the plate during a PET scan may be the same or substantially the same as that in a CT scan. Because the height adjustment unit 34 is installed at a fixed position, the positions of the plate 331 in the FOV may be constant for multiple PET scans. The position error between the height of the plate during a PET scan and the height of the plate in a corresponding CT scan may change. Thus the PET scan data may be corrected separately to compensate the difference of the heights of the plate between the CT imaging mode and the PET imaging mode, in order to make a CT image and a corresponding PET image match. The correction data may be obtained by experiments conducted in advance and stored for future use. In some embodiments, the height of the plate may be adjusted to compensate the difference of the heights of the plate between the CT imaging mode and the PET imaging mode so as to make a CT image and a corresponding PET image match.

In some embodiments, the scan range of the PET unit 32 may be long. For example, a whole body scan may be performed in a single scan.

In the imaging system 30, there is a position 3331 for a CT scan and a position 3332 for PET scan on the base 333 along the z axis. When the bracket 332 is placed at the position 3331 for CT scan, a patient may be placed onto or removed from the table unit 33. In some embodiments, the plate may need to exit from the bore of the CT scanner 31 completely to avoid collision with the CT scanner 31 when the plate 331 is moved up or down. In this case, the distance between one end of the plate 331 close to CT scanner 31 and the scanning cross-section along the z axis may be at least half of the size of the CT scanner 31 in the z axis, for example, about 400 mm. The maximum moving distance of the plate may be 2100 mm or so. The CT scan may not be performed for the patient if the range of the plate 331 movement is within 400 mm as it needs to leave enough distance for the plate 331 to slow down. Thus the maximum scan range of the CT scanner 31 is less than 1700 mm. For a patient who is taller than 1700 mm, the CT scanner 31 may not provide a whole body scan.

PET/CT system 40 according to some embodiments of the present disclosure, may extend the scan range of the CT scanner without changing the size of the imaging system.

Figure 6A:
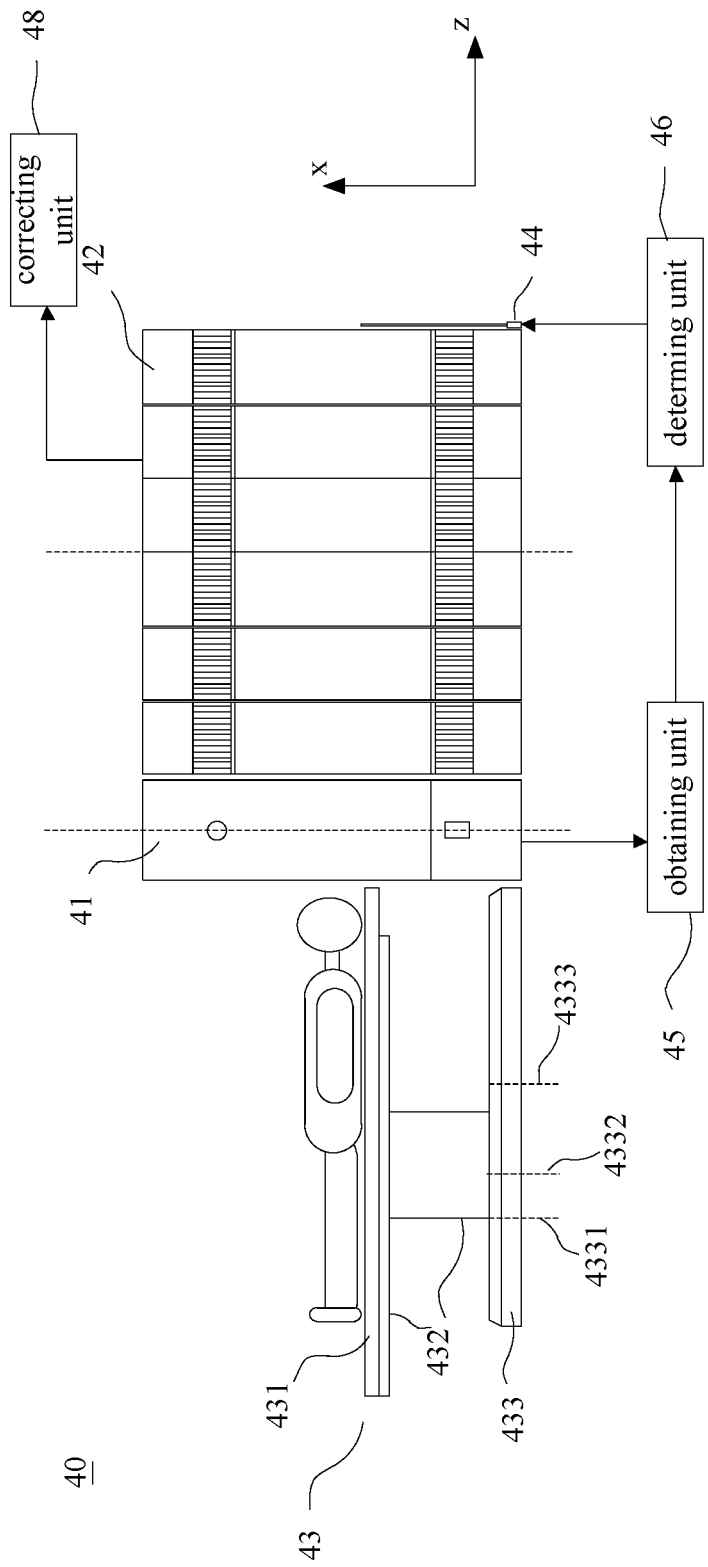
FIG. 6(a) is a diagram illustrating an exemplary PET/CT system according to some embodiments of the present disclosure.
Figure 6B:
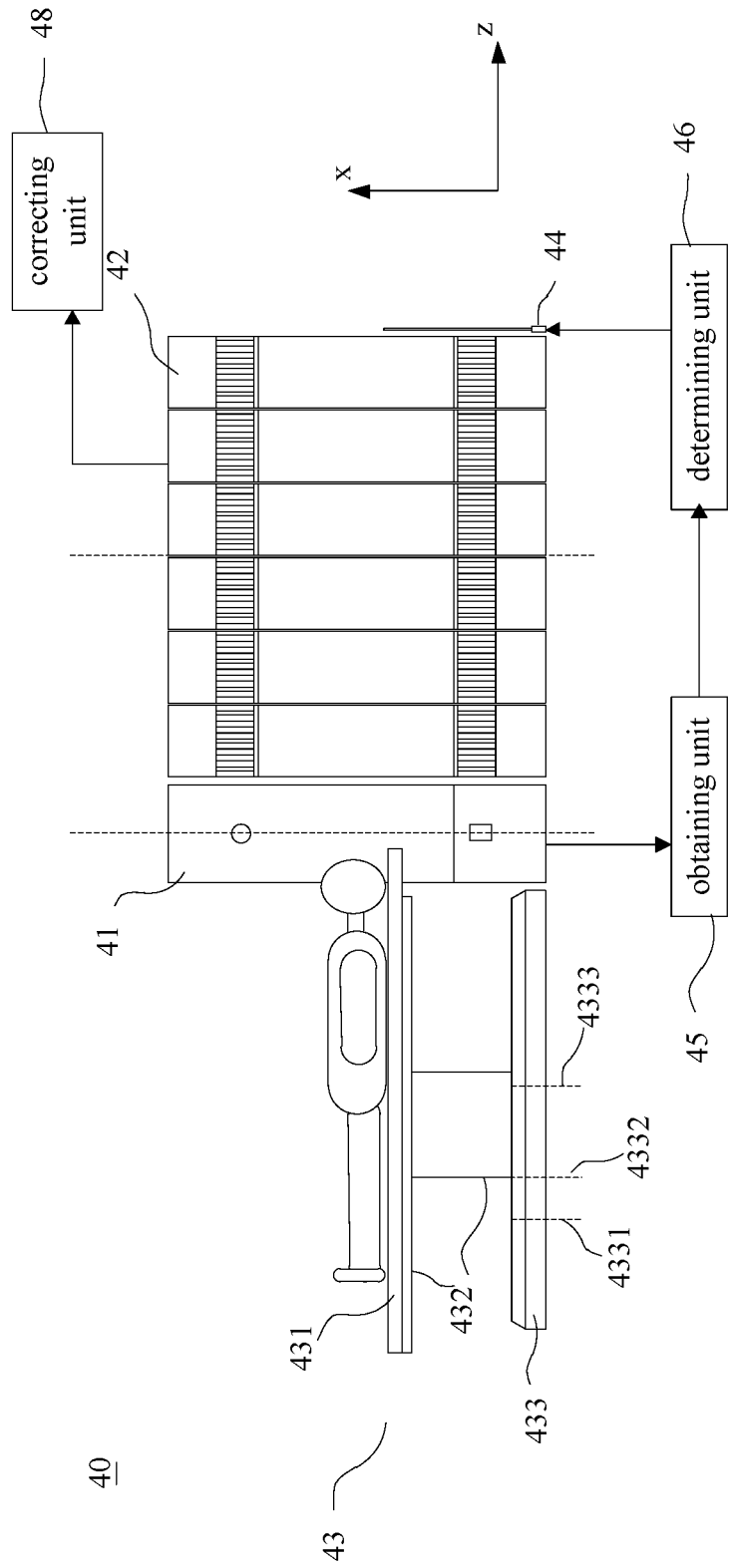
FIG. 6(b) is a diagram illustrating a CT scan performed by the PET/CT system illustrated in FIG. 6(a)
Figure 6C:
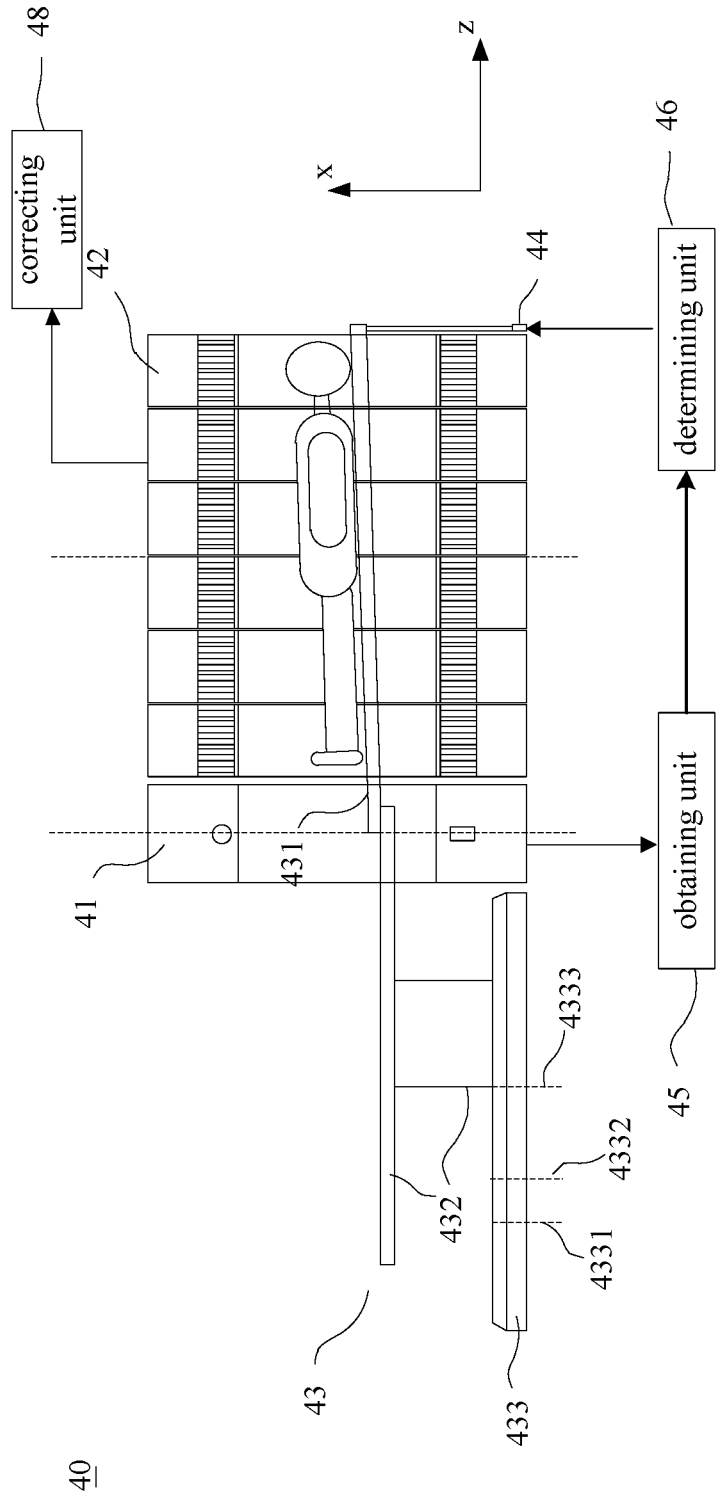
FIG. 6(c) is a diagram illustrating a PET scan performed by the PET/CT system illustrated in FIG. 6(a)

FIG. 6(*a*), FIG. 6(*b*), and FIG. 6(*c*) are diagrams illustrating different states of an exemplary PET/CT system according to some embodiments of the present disclosure. With reference to FIG. 6(*a*), The PET/CT system 40 may include a CT scanner 41, a PET scanner 42, and a table unit 43. In some embodiments, the CT scanner 41 and the PET scanner 42 may be coaxial. In some embodiments, the CT scanner 41 and the PET scanner 42 may be non-coaxial. The table unit 43 may include a base 433, a bracket 432, and a plate 431. The plate 431 may be configured to move relatively to the bracket 432 along a length direction of the plate 431. The PET/CT system of FIG. 6(*a*) through FIG. 6(*c*) may include a releasing position 4331, a CT scan position 4332, and a PET scan position 4333 on the base 433 along the z axis that is parallel to a rotation axis of the CT scanner 41 (i.e., a length direction of the plate 431).

When the bracket 432 is placed at the position 4331, the distance of the plate 431 to move up or down is larger and the plate 431 may move to the position below the bore of the CT scanner 41 for the patient to be placed onto or removed from the table unit 43. When the bracket 432 is placed at the position 4332 (or the position 4333), the distance of the plate 431 to move up or down is shorter than the diameter of the bore of the CT scanner 41 (or the PET scanner 42) to avoid collision.

With reference to FIG. 6(*a*), when the bracket 432 is placed at the position 4331, the plate 431 may exit from the bore of CT scanner 41 completely to avoid collision with CT scanner 41 when the plate 431 is moved up or down. At this time, the distance of the plate 431 for moving in the x axis is larger, and may be the range from 450 mm to 1000 mm, from 500 mm to 1000 mm, from 550 mm to 950 mm, or from 550 mm to 945 mm, wherein the distance may be the distance from the floor in the x axis. The plate 431 may move to a position about 500 mm above the floor, which is convenient for a short patient to get or be placed onto or removed from the table unit 43.

Optionally, when the bracket 432 is placed at the position 4331, if the plate 431 moves in the x axis with a displacement relative to the bracket 432, the alarm may be triggered; optionally, when the bracket 432 is placed at the position 4331, the plate 431 may be unable to move in the x axis with a displacement relative to the bracket 432; optionally, when the bracket 432 is placed at the position 4331, if the distance from the plate 431 to the floor is outside a given range, the plate 431 may move up or down in the x axis but not in the z axis; if the distance from the plate 431 to the floor is within the given range, the plate 431 may move in the z axis; optionally, when the bracket 432 is placed at the position 4331, the plate 431 may move up or down in the x axis but not in the z axis without a displacement relative to the bracket 432. It may improve the safety to avoid the collision due to misoperation at the position 4331.

With reference to FIG. 6(*b*), when the CT scan is to be performed for a patient, the bracket 432 may be placed at the position 4332, and the distance between one end of the plate 431 close to CT scanner 41 and the scanning cross-section in the z axis is short. The speed of the plate 431, referred to as the scan speed, may be low when a CT scan is performed in the CT scanner 41. In FIG. 6(*b*), the distance between one end of the plate 431 close to CT scanner 41 and the scanning cross-section in the z axis is long enough to allow the plate 431 to accelerate to the scan speed. The distance between one end of the plate 431 close to CT scanner 41 and the scanning cross-section in the z axis may be in the range from 20 mm to 200 mm, from 20 mm to 150 mm, from 20 mm to 100 mm, or from 20 mm to 50 mm, etc.

Merely by way of example, the maximum distance for the plate 431 to move in the z axis is about 2100 mm; the maximum distance is assumed to be 2160 mm; the distance between one end of the plate 431 close to CT scanner 41 and the scanning cross-section in the z axis is 50 mm when the bracket 432 is placed at the position 4332. That is, the distance for the plate 431 to accelerate from 0 to the scan speed is 50 mm. The distance for the plate 431 to slow down from the scan speed to 0 is 50 mm when the scan ends. If the scan range is 2000 mm, the distance for the plate 431 to move corresponding to the scan range is 50 mm+2000 mm+50 mm=2100 mm, which is less than the maximum distance 2160 mm. So the PET/CT system 40 may extend the scan range of the CT scanner 41 compared with the PET/CT system 30 in FIG. 3 to FIG. 5.

The maximum scan range of the CT scanner 41 may be determined by the maximum distance for the plate to move, the scan speed and the acceleration of the plate, or the like, or a combination thereof. Suppose the maximum distance for the plate 431 to move is L, the distance for the plate 431 to accelerate from 0 to the scan speed is $S_1$ and the distance for the plate 431 to slow down from the scan speed to 0 is $S_2$, and the maximum scan range of the CT scanner 41 is:

$$L - S_1 - S_2 \qquad (2)$$

In some embodiments, suppose the maximum distance for the plate 431 to move is 2160 mm and the distance for the plate 431 to accelerate or decelerate is 50 mm, the maximum scan range of the CT scanner 41 is 2160 mm−50 mm−50 mm=2060 mm. If the maximum distance for plate 431 to move is 2200 mm, the maximum scan range of the CT scanner 41 is 2100 mm. The maximum scan range of the CT scanner 41 may also be other values, for example, 1700 mm. Without increasing the size of the table unit 43, the maximum scan range of the CT scanner 41 is from 1700 mm to 2100 mm, 2060 mm, 2000 mm, 1960 mm, or 1900 mm, and so the CT scanner 41 may substantially perform a whole body scan for many patients.

When the bracket 432 at the position 4332, the distance for the plate 431 to move in the x axis is shorter and may be the range from 700 mm to 1000 mm, from 750 mm to 1000 mm, from 800 mm to 950 mm, or from 820 mm to 945 mm. As used herein, the distance for the plate 431 to move in the x axis is the distance from the floor in the x axis. The motion range of the plate 431 in the x axis may be limited. When the plate 431 moves in the positive direction of the x axis, the patient may need to be protected from collision with the CT scanner 41; when the plate 431 moves in the negative direction of the x axis, the plate 431 may need to be protected from collision with the CT scanner 41.

With reference to FIG. 6(*c*), when the PET scan is to be performed for a patient, the bracket 432 is placed at the position 4333 and the whole body of the patient is in the FOV of the PET scanner 42 such that the PET scanner 42 may perform a whole body scan in a single scan. The FOV may be related to the size of the PET scanner 42 in the z axis and may be the range from 1700 mm to 2000 mm, from 1800 mm to 2000 mm, or from 1900 mm to 2000 mm, etc.

When the bracket 432 is at the position 4333, the distance for the plate 431 to move in the x axis may be the same as that during the CT scanning or not, provided that the plate 431 or the patient does not collide with the PET scanner 42.

In some embodiments, the distance between one side of the CT scanner 41 and the scanning cross-section in the z axis may be about 400 mm long, and the FOV of the PET scanner 42 may be about 2000 mm long. The distance between the scanning cross-section and the center of the FOV is about 1400 mm. If the distance between position 4332 and position 4333 is 1400 mm, the structure and size of the table unit 43 may need to be changed, which may cause an increase in not only the size of the imaging system but also the cost. So the distance between position 4332 and position 4333 may be different from the distance between the scanning cross-section and the center of FOV of the PET scanner 42.

Compared with the embodiments in FIG. 3 to FIG. 5 in which the distance between one end of the plate 331 close to CT scanner 31 and the scanning cross-section is about 400 mm when the bracket 332 is placed at the position 3331, the distance between one end of the plate 431 close to CT scanner 41 and the scanning cross-section is only about 50 mm when the bracket 432 is placed at the position 4332. If the maximum distance for the plate to move in FIG. 6(*a*), FIG. 6(*b*), or FIG. 6(*c*) is the same as that in FIG. 3 to FIG. 5, the longer distance for the plate 431 of the table unit 43 to move may be used for the CT scan in the embodiments illustrated in FIG. 6(*a*), FIG. 6(*b*), and FIG. 6(*c*). That is, the embodiments illustrated in FIG. 6(*a*), FIG. 6(*b*), and FIG. 6(*c*) may extend the scan range of the CT scanner 41 without increasing the size of the table unit 43.

When the scan range is longer, one unsupported end of the plate 431 may bend with the movement of the plate 431 in the z axis during a CT scan. The farther the plate 431 moves in the z axis, the more seriously the plate 431 bends. The unsupported end of the plate 431 may also bend during a PET scan. From the description of FIG. 1 and FIG. 2, the trends of the bending of the plate in a CT image and a corresponding PET image may be opposite. Thus, the bending of the plate may be compensated by combining the embodiments described with reference to FIG. 6(*a*), FIG. 6(*b*), and FIG. 6(*c*) with the embodiments described with reference to FIG. 3 to FIG. 5, in order to compensate the difference of the bending of the plate between the CT imaging mode and the PET imaging mode.

For example, the PET/CT system 40 may include a height adjustment unit 44 configured to adjust the height of the plate 431 based on the height of the plate 431 at the scanning cross-section during the CT scan so that the changing trend of the height of the adjusted plate 431 during a PET scan is consistent with the changing trend of the height of the plate during the CT scan. To compensate the difference of the bending between the CT imaging mode and the PET imaging mode, the height adjustment unit 44 may be controlled to drive the plate 431. The PET/CT system 40 may further include an obtaining unit 45 and a determining unit 46.

The obtaining unit 45 may be configured to obtain images. The images may be CT images or topograms.

The determining unit 46 may be configured to determine the relationship between the heights of the plate in the images and the distances of the plate moving in the axial direction. In some embodiments, the relationship may be linear or substantially linear. In some embodiments, the relationship may be non-linear.

The height adjustment unit 44 may be configured to adjust the height of the plate based on the relationship to make the movement of the adjusted plate (including, for example, the movement of the plate along the axial direction, the height adjustment, the bending of the plate) fit the relationship. In this case, PET scan data may be obtained by a PET scan. PET images may be obtained by reconstructing the PET scan data. The changing trend of the height of the plate 431 in a PET image may be consistent with the changing trend of the height of the plate in a CT image. There may be a position error of the plate between the CT image and the corresponding PET image for a same slice. The position error may be corrected to compensate the difference of the height of the plate between the CT imaging mode and the PET imaging mode and to make the CT image and the corresponding PET image match.

In some embodiments, the PET/CT system 40 may further include a correcting unit 48 configured to correct the position error of the plate during a PET scan compared to a CT scan.

The position error with respect to loads of different weights may be obtained by experiments and stored. The position error may be acquired directly based on the weight of a patient when needed. Specifically, after a PET scan, the correcting unit 48 may obtain the position error relating to the patient and correct data acquired in the PET scanning. The reconstruction unit of the PET scanner 42 may reconstruct the corrected data to obtain the PET images in which the positions of the plate may match the positions of the plate in CT images. The matching may be obtained by performing a PET scan after the entire plate 431 is adjusted for the position error.

More descriptions may be found elsewhere in the present disclosure. See, for example, the description with reference to FIG. 3 to FIG. 5.

Figure 7:
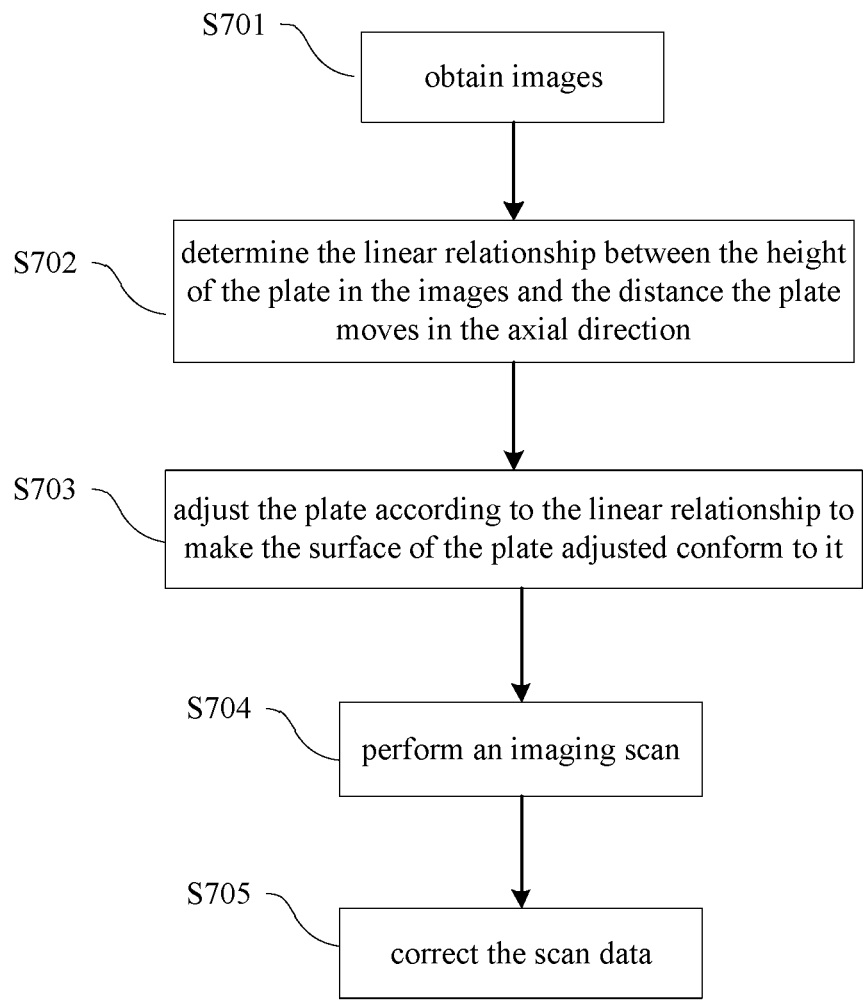
FIG. 7 is a flowchart illustrating an imaging method according to some embodiments of the present disclosure.

FIG. 7 is a flowchart illustrating an imaging process according to some embodiments of the present disclosure.

In step 701, images may be obtained.

The images may be CT images or topograms. In some embodiments, CT images are provided merely for illustration purposes, and not intended to limit the scope of the present disclosure.

In step 702, a relationship between the heights of the plate in the images and the distances of the plate moving in the axial direction may be determined. In some embodiments, the relationship may be linear or substantially linear. In some embodiments, the relationship may be non-linear.

In step 703, the plate may be adjusted according to the relationship, in order to make the movement of the adjusted plate fitting the linear relationship.

The plate may be adjusted according to the linear relationship determined in step 702, in order to make the surface of the plate (including, for example, the movement of the plate along the axial direction, the height adjustment, the bending of the plate) fit the relationship. The distance may be monitored when the plate rises to assess the movement of the plate based on the relationship. The distance by which the plate needs to rise based on the relationship may be determined in advance and then one end of the plate may be raised to make the movement of the plate fit the relationship.

In step 704, an imaging scan may be performed.

In this case, a PET scan may be performed. The problem that the changing trend of the height of the plate in the CT imaging mode is different from that in the PET imaging mode may be solved. PET images may be obtained by reconstructing the PET scan data, in which the changing trend of the height of the plate in the PET images may be consistent with that in the CT images. Image fusion that matches the images obtained in different imaging modes may be simplified.

In some embodiments, there may be a position error of the plate between the PET images and the CT images. The position error may be corrected to compensate the difference of the height of the plate between the CT imaging mode and the PET imaging mode and to make a CT image and a corresponding PET image match. In some embodiments, the imaging process may further include step 705.

In step 705, the scan data may be corrected.

Figure 8:
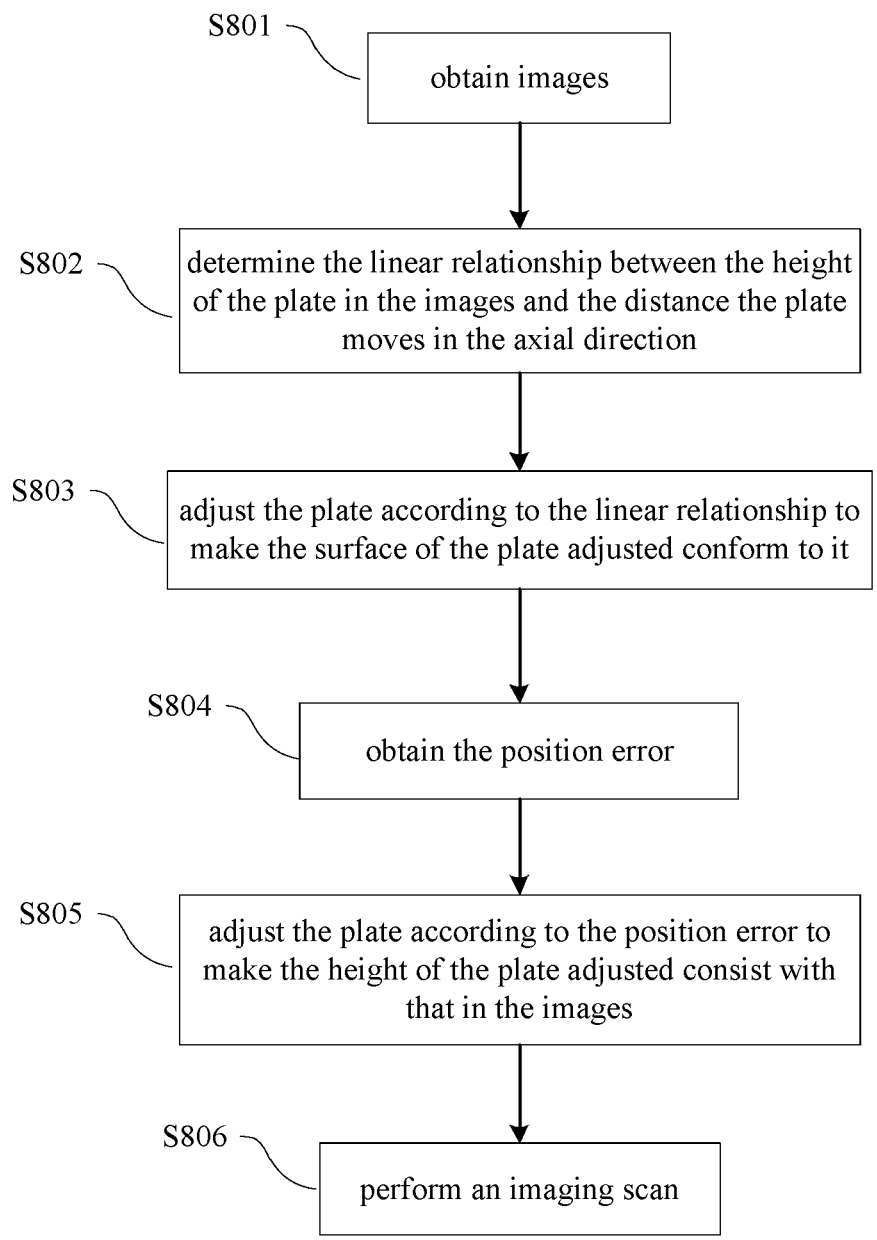
FIG. 8 is a flowchart illustrating another imaging method according to some embodiments of the present disclosure.

The position error may be corrected by lowering the plate directly, as shown in FIG. 8. More descriptions may be found elsewhere in the present disclosure. See, for example, the description with reference to FIG. 3 to FIG. 6.

FIG. 8 is a flowchart illustrating an imaging process according to some embodiments of the present disclosure.

In step 801, the images may be obtained.

The images may be CT images or topograms. In some embodiments, CT images are provided merely for illustration purposes, and not intended to limit the scope of the present disclosure.

In step 802, the relationship between the heights of the plate in the images and the distances of the plate moving in the axial direction may be determined. In some embodiments, the relationship may be linear or substantially linear. In some embodiments, the relationship may be non-linear.

In step 803, the plate may be adjusted according to the relationship, in order to make the movement of the adjusted plate fit the relationship. The movement of the plate may include, for example, the movement of the plate along the axial direction, the height adjustment, the bending of the plate.

In step 804, the position error may be obtained.

In step 805, the plate may be adjusted according to the position error to make the height of the adjusted plate constant in various images.

In step 806, an imaging scan may be performed.

In some embodiments, the position error in step 804 may be obtained before the step 801, which is a variation within the scope of the present disclosure.

More description may be found elsewhere in the present disclosure. See, for example, the description with reference to FIG. 3 to FIG. 6.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "block," "module," "engine," "unit," "component," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the operator's computer, partly on the operator's computer, as a stand-alone software package, partly on the operator's computer and partly on a remote computer or entirely on the remote computer or server. In the latter scenario, the remote computer may be connected to the operator's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities of ingredients, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method comprising:
   obtaining images by scanning a subject placed on a plate of a table in a CT imaging mode;
   determining a linear relationship between height of the plate in the images and distance of the plate moving in a length direction of the plate;
   adjusting the height of the plate according to the linear relationship such that a movement of the adjusted plate fits the linear relationship;
   obtaining a position error of the plate between the CT imaging mode and a PET imaging mode;
   adjusting, according to the position error, the height of the plate in the PET imaging mode; and
   performing, in the PET imaging mode, a PET scan for the subject placed on the adjusted plate.

2. The method of claim 1, wherein the adjusting the height of an end of the plate according to the linear relationship such that a movement of the adjusted plate fits the linear relationship includes:
   determining a raised height according to the linear relationship and a measured distance of the plate moving in the length direction of the plate; and
   adjusting the height of the end of the plate based on the determined raised height.

3. The method of claim 1, wherein the obtaining a position error of the plate between the CT imaging mode and a PET imaging mode includes:
   obtaining the position error from experimental position error data with a water phantom and loads of different weights, wherein the obtained position error corresponds to the load of the weight of the subject.

4. The method of claim 3, wherein the adjusting, according to the position error, the height of the plate in the PET imaging mode includes:
   lowering the height of the plate by the obtained position error.

5. The method of claim 1, wherein the images are CT images or topograms.

6. A PET/CT system comprising:
   a CT scanner configured to perform CT scanning in accordance with a CT imaging mode;
   a PET scanner configured to perform PET scanning in accordance with PET imaging mode;
   a table including a base, a bracket, and a plate movable relative to the bracket;
   at least one computer readable medium including executable instructions; and
   at least one processor in communication with the executable instructions, wherein when executing the executable instructions, the at least one processor is configured to cause the system to perform operations including:
   obtaining images by scanning a subject placed on the plate of the table in the CT imaging mode;
   determining a linear relationship between height of the plate in the images and distance of the plate moving in a length direction of the plate;
   adjusting the height of the plate according to the linear relationship such that a movement of the adjusted plate fits the linear relationship;
   obtaining a position error of the plate between the CT imaging mode and the PET imaging mode;
   adjusting, according to the position error, the height of the plate in the PET imaging mode; and
   performing, in the PET imaging mode, the PET scan for the subject placed on the adjusted plate.

7. The PET/CT system of claim 6, wherein the adjusting the height of an end of the plate according to the linear relationship such that a movement of the adjusted plate fits the linear relationship includes:
   determining a raised height according to the linear relationship and a measured distance of the plate moving in the length direction of the plate; and
   adjusting the height of the end of the plate based on the determined raised height.

8. The PET/CT system of claim 6, wherein the obtaining a position error of the plate between the CT imaging mode and a PET imaging mode includes:
   obtaining the position error from experimental position error data with a water phantom and loads of different weights, wherein the obtained position error corresponds to the load of the weight of the subject.

9. The PET/CT system of claim 8, wherein the adjusting, according to the position error, the height of the plate in the PET imaging mode includes:

lowering the height of the plate by the obtained position error.

10. The PET/CT system of claim 6, wherein the images are CT images or topograms.

11. The PET/CT system of claim 6, wherein the base includes a releasing position, a CT scan position and a PET scan position.

12. The PCT/CT system of claim 11, wherein a distance of the plate to move up or down when the bracket is placed at the releasing position of the base is larger than a distance of the plate to move up or down when the bracket is placed at the CT scan position of the base.

13. The PCT/CT system of claim 11, wherein when the bracket is placed at the PET scan position of the base, the plate is movable for a distance from a floor on which the table is placed the same as the distance for the plate to move from the floor when the bracket is placed at the CT scan position.

14. The PCT/CT system of claim 11, wherein the plate is movable for a distance from a floor on which the table is placed in a range from 500 mm to 1000 mm when the bracket is placed at the releasing position of the base.

15. The PCT/CT system of claim 11, wherein the plate is movable for a distance from the floor in a range from 750 mm to 1000 mm when the bracket is placed at the CT scan position.

16. A method comprising:

obtaining images by scanning a subject placed on a plate of a table in a CT imaging mode;

determining a linear relationship between height of the plate in the images and distance of the plate moving in a length direction of the plate;

adjusting the height of an end of the plate according to the linear relationship such that a movement of the adjusted plate fits the linear relationship; and performing, in a PET imaging mode, a PET scan for the subject placed on the adjusted plate.

17. The method of claim 16, further comprising:

correcting, based on a position error between the CT imaging mode and the PET imaging mode, scan data acquired in the PET scanning.

18. The method of claim 17, further comprising:

reconstructing a PET image based on the corrected scan data.

19. The method of claim 17, wherein the position error is obtained from experimental position error data with a water phantom and loads of different weights, the obtained position error corresponding to the load of the weight of the subject.

20. The method of claim 16, wherein the images are CT images or topograms.

* * * * *